United States Patent [19]

Hickmann et al.

[11] 3,998,712
[45] Dec. 21, 1976

[54] MONOKETAL OF DIKETONES AS SENSITIZER FOR U.V. POLYMERIZABLE SYSTEMS

[75] Inventors: Eckhard Hickmann, Ludwigshafen; Martin Fischer, Ellerstadt; Milan Velic; Otto Volkert, both of Ludwigshafen, all of Germany

[73] Assignee: Badische Anilin- & Soda-Fabrik Aktiengesellschaft, Ludwigshafen (Rhine), Germany

[22] Filed: June 29, 1973

[21] Appl. No.: 375,075

[30] Foreign Application Priority Data

July 1, 1972    Germany .................... 2232365

[52] U.S. Cl. .............. 204/159.15; 96/35.1; 96/115 R; 96/115 P; 204/159.12; 204/159.23; 260/17.4 GC; 260/28.5 R; 260/37 N; 260/40 R; 260/42.21; 260/590 D; 260/857 G; 260/859 R; 260/861; 260/866; 260/869; 260/874; 260/901; 427/54
[51] Int. Cl.² .............. C08F 8/00; C08F 2/48; G03C 1/68; G03C 5/08
[58] Field of Search .............. 204/159.15, 159.22, 204/159.23, 159.12; 260/80 C, 78.4 A, 590; 96/115 R, 115 P, 35.1

[56] References Cited

UNITED STATES PATENTS

| | | | |
|---|---|---|---|
| 3,010,945 | 11/1961 | Ikeda | 260/78.4 A |
| 3,225,014 | 12/1965 | D'Alelio | 204/159.23 |
| 3,357,962 | 12/1967 | Hopff et al. | 204/159.23 |
| 3,582,487 | 6/1971 | Fuhr et al. | 204/159.23 |

*Primary Examiner*—Murray Tillman
*Assistant Examiner*—Thurman K. Page
*Attorney, Agent, or Firm*—Johnston, Keil, Thompson & Shurtleff

[57] ABSTRACT

Compositions polymerizable by ultraviolet irradiation which contain photopolymerizable monomers possessing at least one polymerizable carbon-carbon multiple bond and monoketals of the formula

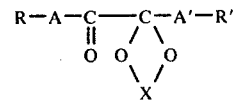

as photoinitiators. The compositions have a particularly long shelf life and show very little yellowing after curing by irradiation.

7 Claims, No Drawings

MONOKETAL OF DIKETONES AS SENSITIZER FOR U.V. POLYMERIZABLE SYSTEMS

The invention relates to compositions which contain special photoinitiators and are polymerizable by ultraviolet irradiation, and to the use of the compositions.

Compositions which are polymerizable by ultraviolet irradiation, and contain compounds with polymerizable carbon-carbon multiple bonds, or mixtures of such compounds with polymers and other customary additives, such as inhibitors, dyestuffs and the like, and photoinitiators, that is to say compounds which initiate and accelerate the photopolymerization, are known and have a variety of uses for example for the production of coatings or for information fixing, for example for the production of photopolymer printing plates, especially of relief printing plates. A large number of photoinitiators have been proposed for such compositions and some have also been used in practice, examples being quinones, α-diketones, acyloins and their derivatives, azo, diazo and diazonium compounds or chromates and dichromates. However, a series of inherent disadvantages limit the practical applicability of the photoinitiators which have been proposed. Thus, the solubility of chromates, dichromates and other inorganic initiators in the photopolymerizable compositions is frequently inadequate. α-diketones such as benzil or diacetyl are insufficiently reactive for many purposes and other initiator systems such as quinones, sulfur compounds, halogen compounds or metalcarbonyl complexes are easily inhibited by oxygen. Azo, diazo and diazonium compounds are easily decomposed by heat. Acyloins and some of their derivatives are not quite sufficiently stable for some purposes. Benzoin derivatives in practice easily produce yellowing in photocuring photopolymerizable compositions and this is a considerable disadvantage, for example when producing coatings. Hence there is a need for photopolymerizable compositions, containing photoinitiators, which are stable under the customary processing conditions and also do not decompose on storage, but are still sufficiently reactive and produce as little yellowing as possible.

We have now found that compositions which are polymerizable by ultraviolet irradiation and contain compounds with at least one photopolymerizable carbon-carbon multiple bond or mixtures of such compounds, a photoinitiator and, optionally, customary additives, have very advantageous properties for numerous end uses if the photoinitiators which they contain are monoketals of diketones of the formula

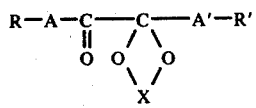

where R and R' are H or Cl or $C_1$-$C_4$-alkyl, $C_1$-$C_4$-alkoxy or $C_1$-$C_4$-alkoxyalkyl radicals of identical or different type, X is $C_nH_{2n}$ with n being 2 to 8 and A and A' are six-membered aromatic radicals of identical or different type.

Photoinitiators in which A and/or A' are phenyl or phenylene and X is ethylene, propylene or butylene are very suitable. Particularly preferred compounds are the monoketals of benzil, 2,2'-dichlorobenzil and 4,4'-dichlorobenzil and especially the monoketals with aliphatic diols with 2 to 8 carbon atoms, such as ethylene glycol, propylene-1,2 glycol, propylene-1,3 glycol, butylene-1,2 glycol, butylene-1,3 glycol, butylene-2,3 glycol and neopentyl glycol (2,2-dimethylpropylene-1,3 glycol), above all the corresponding monoketals of benzil.

One method of making monoketals of 1,2-diketones is described, for example, in J. Amer. Chem. Soc. 81 (1959) 633 to 639. The cyclic monoketals, mentioned above, which can be manufactured by this process from the 1,2-diketones mentioned and 1,2- or 1,3-glycols mentioned, (that is to say, 1,3-dioxolane or 1,3-dioxane derivatives) have the advantage, amongst others, over the open-chain monoketals which are derived from the same 1,2-diketones and monohydric alcohols or phenols, that they are much more readily obtainable. Whilst in the case of the cyclic compounds the ketalization can be carried out by a well-established process with cheap starting substances (as in the acid-catalyzed ketalization of ketones with glycols) it is necessary, when manufacturing the open-chain compounds, to resort to expensive starting substances (alkyl iodides and barium oxide; compare R. Kuhn and H. Trischmann, Ber., 94, 2,258 (1961). Furthermore, in the latter case the yield is unsatisfactory due to losses of material during the involved purification operations which have to be carried out (such as extraction, washing with water and sodium thiosulfate solution, distillation in a high vacuum or crystallization). Furthermore, the formation of an undesirable byproduct of the type of benzilic acid must be expected if the barium oxide used is contaminated with barium hydroxide or if one of the starting substances is moist.

In general, the monoketals of the 1,2-diketones, which have been mentioned, are used in amounts of 0.01 to 10% by weight and preferably of 0.05 to about 4% by weight, relative to the photosensitive composition or the photopolymerizable compounds.

All compounds having at least one carbon-carbon multiple bond which can, in admixture with the photoinitiator, be activated so as to undergo a photopolymerization, are suitable for use in the compositions in question. Monomers and substances with carbon-carbon double bonds which are activated by, for example, aryl, carbonyl, amide, ester, carboxyl or nitrile groups, halogen atoms or carbon-carbon double bonds or carbon-carbon triple bonds, are very suitable. Examples which may be mentioned are styrene, vinyltoluene, acrylic acid and methacrylic acid and their esters, nitriles or amides, for example acrylamide, N-methylolacrylamide, diethers of 1 mole of glycol and 2 moles of N-methylolacrylamide, methyl methacrylate, methylene-bis-acrylamide, m-phenylene-bis-acrylamide and m-xylylenebis-acrylamide.

The photopolymerizable compounds can readily be chosen by those skilled in the art to suit the particular end use of the compositions and can contain, in a known manner, unsaturated and/or saturated polymers and/or the known additives, such as inhibitors against thermal polymerization, for example hydroquinone or tert.-butylhydroquinone, skinforming substances such as paraffin, flow improvers such as silicone oil, fillers and/or pigments or dyestuffs, these substances being added in the customary amounts. Such compositions are known to those skilled in the art and the nature and amount of the additives depend in particular on the end use of the compositions.

Amongst the compositions of the invention, unsaturated polyester resins containing the monoketals as photoinitiator have proved particularly successful in the production of coatings which can be cured with ultraviolet radiation. Suitable compositions of unsaturated polyester resins consist, for example, for a mixture of (1) 40 to 80 per cent by weight of an unsaturated polyester of a customary type, (2) 60 to 15 per cent by weight of at least one copolymerizable olefinically unsaturated monomer, (3) 0.5 to 5 per cent by weight of a photoinitiator and, if desired, (4) further customary additives.

Suitable unsaturated polyesters (1) for this purpose are the customary polycondensation products of polybasic, especially dibasic, carboxylic acids which are linked by ester bonds to polyhydric, especially dihydric, alcohols, and which optionally additionally contain radicals of monobasic carboxylic acids and/or radicals of monohydric alcohols and/or radicals of hydroxycarboxylic acids. These unsaturated polyesters can be manufactured from their components in the usual way, by condensation in the melt or condensation under azeotropic conditions.

Suitable polyhydric, especially dihydric, optionally unsaturated alcohols for the manufacture of the polyesters are the usual alkanediols which in particular contain acyclic groups, cyclic groups or both types of groups, such as ethylene glycol, propylene-(1,2) glycol, butylene-(1,3) glycol, butanediol-(1,4), hexanediol-(1,6), diethylene glycol, triethylene glycol and neopentyl glycol. The polyhydric, especially dihydric, alcohols are in general reacted in stoichiometric amounts with polybasic, especially dibasic, carboxylic acids or their derivatives which can undergo condensation.

Carboxylic acids, or their derivatives, which are suitable for the manufacture of polyesters are dibasic, olefinically unsaturated, carboxylic acids such as, for example, maleic acid, fumaric acid, fumaric acid, itaconic acid, citraconic acid and mesaconic acid and their anhydrides. The polyester can additionally contain other, co-condensed, dibasic unsaturated and/or saturated carboxylic acids, such as, for example, succinic acid, glutaric acid, adipic acid, sebacic acid, phthalic acid and phthalic anhydride, isophthalic acid, terephthalic acid, 1,2,3,6-tetrahydrophthalic acid and 3,6-endomethylene-1,2,3,6-tetrahydrophthalic acid, and also monobasic and tribasic carboxylic acids and carboxylic acids of higher basicity, such as, for example, propionic acid, 1,2,4-benzenetricarboxylic acid or 1,2,4,5-benzenetetracarboxylic acid.

Suitable olefinically unsaturated monomeric compounds (2) for use in the unsaturated polyester resins are all customary monomeric compounds which can be copolymerized with unsaturated polyesters, especially vinylaromatic compounds, such as styrene, and esters of acrylic acid or methacrylic acid with alkanols containing 1 to 8 carbon atoms, such as tert.-butyl acrylate or methyl methacrylate, and mixtures of these monomers. In the preferred compositions the component (2) accounts for 60 to 15 per cent by weight, preferably 50 to 25 per cent by weight.

The compositions of the invention can futhermore be used in photopolymerizable compositions which are suitable for the production of systems in which information is fixed by optical means, especially for the production of photopolymer printing plates. Suitable compositions containing compounds with at least one polymerizable carbon-carbon multiple bond are those which contain about 10 to 60% by weight, and preferably 20 to 35% by weight, of monomers which predominantly have at least two photopolymerizable carbon-carbon multiple bonds, such as diacrylates, dimethacrylates, bisacrylamides and bismethacrylamides of aliphatic or aromatic diamines with 2 to 8 carbon atoms, and monomers which optionally contain urethane or urea groups in addition to amide groups, and 90 to 40% by weight, and preferably 80 to 65% by weight, of a compatible polymer soluble in an organic solvent, such as an alcohol, a ketone or an ether. Examples of polymers which can be used are copolyamides, such as copolyamides of ε-caprolactam, hexamethylene-diammonium adipate adipate and p,p'-diaminodicyclohexylmethane adipate, and also soluble polyurethans, polyureas, polyethers or soluble cellulose derivatives. Suitable compositions of these types and their processing are described in the patent literature, in particular in British Patents 1,154,384, 1,173,074 and 1,191,177 or Belgian Patent 794,260.

The radiation sources used for the light which initiates the polymerization are sources which emit light of wavelengths between 230 and 450 nm. Above all, they are radiation sources with emission maxima in the range of 300 to 380 nm or sources which emit a sufficiently high proportion of light in this wavelength range. Mercury medium pressure lamps are particularly suitable, but mercury high pressure lamps and mercury low pressure lamps as well as superactinic fluorescent tubes can also be used. The lamps mentioned can be doped, if appropriate.

In addition to being suitable for the production of coatings, especially coatings based on polyester resins, the compositions of the invention are suitable for the production of photopolymer printing plates, the production of holograms, photoresist lacquers and poromeric sheets, for the fixing of information generally, and for printing inks which can be cured with ultraviolet light. The compositions of the invention display very long shelf life compared to known photoinitiator systems. Thus, for example, a polyester resin containing benzil-ethylene-ketal has practically twice as long a shelf life as an identical polyester resin containing, for example, α-methylolbenzoin methyl ether, and at the same time coatings prepared therewith and cured with ultraviolet light show very markedly less tendency to yelllow. The improved heat stability is demonstrated, for example, by comparing the ratios $K_{phot.}/k_{therm.}$, determined at 50° for a monomer/photoinitiator system of the same type, this being the ratio of the velocity constants of photochemical decomposition ($k_{phot.}$) and of thermal decomposition ($k_{therm.}$); $k_{phot.}/k_{therm.}$ was 180 when using benzoin, 7,500 when using benzoin methyl ether, 7,800 when using benzoin isopropyl ether, 13,600 when using α-methylolbenzoin methyl ether, 18,000 when using benzil-ethyleneketal and 22,000 when using benzil-neopentylene-ketal.

The parts and percentages mentioned in the Examples and comparative experiments which follow are parts and percentages by weight.

EXAMPLE 1

An unsaturated polyester is manufactured by esterifying 431 parts of maleic anhydride and 325 parts of phthalic anhydride with 525 parts of 1,2-propylene glycol. After adding 0.01% of hydroquinone, a 66% strength solution of the polyester in styrene is prepared (Solution A).

97 parts of this unsaturated polyester resin are mixed with 3 parts of benzil-ethylene-ketal (Solution B).

The shelf life (gel point) of this mixture is determined at 60° C, in the absence of light. The results are summarized in Table I.

For the photocuring experiments, 10 parts of a 1% strength solution of paraffin (softening range 50° to 52° C) in styrene were added to 100 parts of Solution B and the resin was applied to glass plates or to chipboard sheets, covered with photographic paper, by means of a film spreader with a 400 μm gap. After allowing evaporation for about one minute, the films were exposed for 5 minutes to fluorescent lamps (Philips TLA 05/40 W), mounted at a distance of 4 cm. The color measurements of the lacquer films are summarised in Table I.

EXAMPLE 2

97 parts of the unsaturated polyester resin described in Example 1 are mixed with 3 parts of the monoketal of benzil and neopentyl glycol.

Table I shows the results of determining the shelf life and the color measurements after processing and exposure as in Example 1.

EXAMPLE 3

97 parts of the unsaturated polyester resin described in Example 1 are mixed with 3 parts of benzil-dimethyl-ketal.

Table I shows the results of determining the shelf life and the color measurements after processing and exposure as in Example 1.

Comparative experiments 1 and 2

The procedure of Example 1 is followed precisely, but instead of using benzil-ethylene-ketal, an identical amount of benzoin isopropyl ether (comparative experiment 1) or α-methylolbenzoin methyl ether (comparative experiment 2) is used. Table I shows the results of the determination of the shelf life and of the color measurements. It is found that the compositions of the invention have a longer shelf life and show far less yellowing.

Table I

| Resin from | Shelf life at 60° C [hours] | additionally stabilized with 0.02% of toluhydroquinone | Color measurement of the film; Yellowness Index 5 hours after photocuring |
|---|---|---|---|
| Example 1 | 350 | 1,500 | 8.2 |
| Example 2 | 280 | 1,250 | 7.0 |
| Example 3 | 60 | 220 | 12.8 |
| Comparative experiment 1 | 90 | 380 | 16.3 |
| Comparative experiment 2 | 190 | 730 | 16.5 |

EXAMPLE 4

1 part of benzil-ethylene-ketal is added to a solution of 60 parts of a polyamide of about equal parts of hexamethylenediammonium adipate, 4,4'-diaminodicyclohexylmethane adipate and ε-caprolactam, which is soluble in aqueous alcohol, 30 parts of the diether from 2 moles of N-methylolacrylamide and 1 mole of ethylene glycol and 0.02 part of the potassium salt of N-nitroso-N-cyclohexylhydroxylamine. The solution is cast to give a film and the latter is pressed onto a metallic substrate provided with a light-absorbing adhesive coating.

The coated, light-sensitive plate is exposed over its surface in contact with a negative. Fluorescent tubes with a high proportion of ultraviolet light, at a distance of 3 cm from the plate to be exposed, are used as the light source. After exposure, the unexposed parts of the plate are dissolved out with a mixture of 80 parts of ethanol and 20 parts of water. After drying, a printing plate with a sharp relief is obtained.

EXAMPLE 5

Examples 4 is repeated except that instead of the benzilethylene-ketal the same amount of benzil-neopentylene-ketal is used as the photoinitiator. This allows the exposure time to be reduced to 8 minutes. The sharp reliefs obtained give excellent prints.

EXAMPLE 6

The example which follows is intended to illustrate the use of the photoinitiators according to the invention for printing inks which cure in ultraviolet light:

A photocuring binder is prepared from 60 parts of Grinding Base (a registered trade name of a product manufactured by Lawter Chemicals, Chicago), 80 parts of mineral oil varnishes (consisting of 32 parts of Pentalyn K (a registered trade name of a product manufactured by Hercules Powder, Wilmington) and 48 parts of Samentor 33 (a registered trade name of a product manufactured by Esso AG, Hamburg)), 36 parts of dibutyl maleate, 8 parts, of benzilethylene-ketal and 0.4 part of paraffin oil.

37 parts of the green pigment Heliogen Green (a registered trade name) are added to this binder and the mixture is intimately ground. The resulting printing ink is fed into a commercially available small offset printing machine. A water-cooled 4.4 kW mercury high pressure lamp (Model Q 4,420 Z₃ of Hanau Quarzlampen GmbH) is mounted at a distance of 20 cm above the paper stacker of the printing machine. 3,000 prints are manufactured, the printing speed being adjusted so that each sheet is exposed to the lamp for 1.2 seconds. The printed image is nontacky under a load of 0.1 kg/cm² and under this load no transfer of ink to the sheet above it is detectable.

EXAMPLE 7

The procedure of Example 6 is followed but instead of benzilketal, benzil-neopentylene-ketal is used as the photoinitiator.

Using an exposure time of 1.0 second, practically the same results as in Example 1 are achieved.

We claim:

1. Compositions capable of being cured by ultraviolet irradiation comprising compounds having at least one carbon-carbon multiple bond polymerizable under the action of ultraviolet irradiation, or mixtures of such compounds, and as a photoinitiator, a monoketal of a diketone of the formula

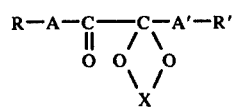

wherein R and R' are H or Cl, or $C_1$-$C_4$-alkyl, $C_1$$C_4$-alkoxy or $C_1$-$C_4$-alkoxyalkyl of identical or different type, X is $C_nH_{2n}$ with n being 2 to 8 and A and A' are six-membered aromatic radicals of identical or different type in a sufficient amount of said photoinitiator to initiate and accelerate the polymerization of said carbon-carbon multiple bonds upon exposure to ultraviolet irradiation, said amount being 0.01 to 10% by weight relative to said photosensitive compositions.

2. Compositions capable of being cured by ultraviolet irradiation, according to claim 1, consisting essentially of a mixture of 0.5–5% of one of said monoketals, 40–80% of an olefinically unsaturated polyester 15–16% of a copolymerizable monomer having at least one polymerizable carbon-carbon double bond.

3. Compositions capable of being cured by ultraviolet irradiation according to claim 1, consisting essentially of a mixture of (1) one of said monoketals, (2) at least one monomer having at least two photopolymerizable carbon-carbon double bonds or a mixture of olefinically unsaturated monomers containing monomers having at least two photopolymerizable carbon-carbon double bonds and (3) at least one compatible saturated polymer, the amount of said monoketal being sufficient to initiate and accelerate polymerization of said carbon-carbon double bonds upon exposure of the composition to ultraviolet irradiation.

4. Compositions capable of being cured by ultraviolet irradiation, according to claim 1, which contain monketals of benzil.

5. Compositions as claimed in claim 1 wherein said compounds having at least one carbon-carbon multiple bond are polymerizable monomers with carbon-carbon double bonds activated by aryl, carbonyl, amide, carboxy ester, or nitrile groups, halogen atoms, or other carbon-carbon double bonds.

6. Compositions as claimed in claim 1 embodied in photopolymer printing plates with a compatible polymer soluble in an organic solvent in an amount of 10 to 60% by weight of monomers which predominantly have at least two photopolymerizable carbon-carbon multiple bonds and 90-40% by weight of said compatible polymer.

7. Compositions as claimed in claim 1 embodied in a coating composition containing, as said compounds having at least one carbon-carbon multiple bond, an unsaturated polyester resin containing carbon-carbon double bonds.

* * * * *

UNITED STATES PATENT AND TRADEMARK OFFICE
CERTIFICATE OF CORRECTION

PATENT NO. : 3,998,712
DATED : December 21, 1976
INVENTOR(S) : Eckhard Hickmann et al.

It is certified that error appears in the above-identified patent and that said Letters Patent are hereby corrected as shown below:

In Column 3, Line 62, delete " ... can futhermore ... " and substitute -- ... can furthermore ... --

In Column 4, Line 47, delete " yelllow. ... " and substitute -- yellow. ... --

In Column 7, Lines 8 and 9, delete " ... polyester 15-16% of ... " and substitute -- ... polyester and 15-60% of ... --

Signed and Sealed this

Seventh Day of June 1977

[SEAL]

Attest:

RUTH C. MASON
Attesting Officer

C. MARSHALL DANN
Commissioner of Patents and Trademarks